United States Patent
Jones et al.

(10) Patent No.: US 8,627,818 B2
(45) Date of Patent: *Jan. 14, 2014

(54) SEALED CAPSULE INCLUDING AN INTEGRATED PUNCTURING MECHANISM

(71) Applicant: Manta Devices, LLC, Roslindale, MA (US)

(72) Inventors: Andrew Jones, Roslindale, MA (US); Richard L. Miller, Needham, MA (US)

(73) Assignee: Manta Devices, LLC, Roslindale, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,567

(22) Filed: Dec. 28, 2012

(65) Prior Publication Data

US 2013/0112200 A1    May 9, 2013

Related U.S. Application Data

(63) Continuation of application No. 12/973,095, filed on Dec. 20, 2010, now Pat. No. 8,342,176, which is a continuation of application No. 10/831,381, filed on Apr. 23, 2004, now Pat. No. 7,861,712.

(51) Int. Cl.
    *B65B 1/04* (2006.01)
(52) U.S. Cl.
    USPC ........................................ 128/203.15; 222/81
(58) Field of Classification Search
    USPC ............ 128/203.15; 222/80, 81, 83; 206/461, 206/469, 531, 532
    See application file for complete search history.

(56) References Cited

U.S. PATENT DOCUMENTS

| | | | |
|---|---|---|---|
| 2,307,986 A | 1/1943 | Bolte et al. |
| 2,860,638 A | 11/1958 | Bartolomeo |
| 2,974,787 A | 3/1961 | Cooper |
| 2,893,392 A | 6/1976 | Gerstel et al. |
| 4,601,896 A | 7/1986 | Nugent |
| 5,035,237 A | 7/1991 | Newell et al. |
| 5,167,242 A | 12/1992 | Turner et al. |
| 5,400,808 A | 3/1995 | Turner et al. |
| 5,476,093 A | 12/1995 | Lankinen |
| 5,501,236 A | 3/1996 | Hill et al. |
| 5,562,918 A | 10/1996 | Stimpson |
| 5,622,166 A | 4/1997 | Eisele et al. |
| 5,669,378 A | 9/1997 | Pera et al. |
| 5,673,793 A | 10/1997 | Seidler |
| 5,921,237 A | 7/1999 | Eisele et al. |
| 5,954,204 A | 9/1999 | Grabowski |

(Continued)

FOREIGN PATENT DOCUMENTS

DE    4400083    7/1995
GB    1211168 A    11/1967

(Continued)

*Primary Examiner* — Steven Douglas
(74) *Attorney, Agent, or Firm* — Wolf, Greenfield & Sacks, P.C.

(57) ABSTRACT

A sealed self-piercing capsule for storing and delivering a substance, such as a medicine, comprises one or more barrier layers forming a sealed chamber for containing the substance. An internal puncturing mechanism is disposed within the capsule chamber for puncturing a barrier layer to release the substance from the chamber. The internal puncturing mechanism may comprise a sharpened edge located on a movable tube, which moves relative to a barrier layer forming the sealed chamber to puncture the barrier layer.

15 Claims, 13 Drawing Sheets

(56) References Cited

U.S. PATENT DOCUMENTS

| | | | |
|---|---|---|---|
| 6,029,663 A | 2/2000 | Eisele et al. |
| 6,089,228 A | 7/2000 | Smith et al. |
| 6,209,538 B1 | 4/2001 | Casper et al. |
| 6,328,034 B1 | 12/2001 | Eisele et al. |
| 6,401,712 B1 | 6/2002 | Von Schuckmann |
| 6,443,307 B1 | 9/2002 | Burridge |
| 6,550,477 B1 | 4/2003 | Casper et al. |
| 6,655,381 B2 | 12/2003 | Keane et al. |
| 6,810,872 B1 | 11/2004 | Ohki et al. |
| 6,941,947 B2 | 9/2005 | Young et al. |
| 7,143,765 B2 | 12/2006 | Asking et al. |
| 7,401,713 B2 | 7/2008 | Ede et al. |
| 7,861,712 B2 * | 1/2011 | Jones et al. | 128/203.15 |
| 8,342,176 B2 * | 1/2013 | Jones et al. | 128/203.15 |
| 2001/0029948 A1 | 10/2001 | Ingle et al. |
| 2002/0006316 A1 | 1/2002 | Schuler et al. |
| 2002/0020408 A1 | 2/2002 | Knauer |
| 2002/0092523 A1 | 7/2002 | Connelly et al. |
| 2003/0034271 A1 | 2/2003 | Burridge |
| 2004/0236282 A1 | 11/2004 | Braithwaite |
| 2006/0169278 A1 | 8/2006 | Djupesland et al. |
| 2007/0023381 A1 | 2/2007 | Cerveny |
| 2007/0074721 A1 | 4/2007 | Harmer et al. |
| 2008/0314384 A1 | 12/2008 | Harris et al. |
| 2009/0250057 A1 | 10/2009 | Wachtel et al. |

FOREIGN PATENT DOCUMENTS

| | | |
|---|---|---|
| GB | 2405798 A | 3/2005 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 02/098495 A1 | 12/2002 |
| WO | WO 03/000326 A1 | 1/2003 |
| WO | WO 03/015857 A1 | 2/2003 |
| WO | WO 2005/002654 A3 | 1/2005 |
| WO | WO 2005/025656 A1 | 3/2005 |
| WO | WO 2005/030305 A1 | 4/2005 |

* cited by examiner

SEALED CAPSULE INCLUDING AN INTEGRATED PUNCTURING MECHANISM

RELATED APPLICATIONS

This application is a continuation of U.S. application Ser. No. 12/973,095, filed on Dec. 20, 2010, which is a continuation of U.S. application Ser. No. 10/831,381, filed on Apr. 23, 2004, which applications are hereby incorporated by reference in their entirety.

FIELD OF THE INVENTION

The present invention relates to a delivery and packaging device for substances, such as medicines. The present invention is particularly useful for the administration of medicine by inhalation.

BACKGROUND OF THE INVENTION

Various drugs in dry powder form may be inhaled directly into the lungs through the mouth or nose. Inhalation allows the drug to bypass the digestive system and may eliminate the need for other more invasive drug application techniques, such as hypodermic injections. Direct inhalation can also allow smaller doses of a drug to be used to achieve the same desired results as the same drug taken orally. Inhalation can also help avoid certain undesirable side effects associated with taking a medicine orally or by injection.

One form of delivery device that is employed for inhaling a drug is the pressurized aerosol or metered dose inhaler (MDI). MDI's are, however, not suitable for use by all patients, e.g., small children, or for the administration of all medicaments. In addition, MDI's use propellants that can cause environmental damage. A widely used alternative is the so-called dry powder inhaler in which medicament powder is dispensed from an elongate gelatin capsule by causing the capsule to rotate and/or vibrate in an airstream, releasing the medicament that is inhaled by the patient. The capsules may be pierced by a suitable puncturing mechanism to release the medicament, or the capsules may be supplied in pre-pierced form. Additional packaging that prevents loss of powder from the capsule and the ingress of moisture is often necessary.

Gelatin capsules, and known drug delivery devices for inhalation, suffer from numerous disadvantages. For example, gelatin capsules are not impervious to moisture so exposure to the atmosphere can result in absorption of moisture. This may lead to agglomeration of the medicament powder particles. These problems may be particularly acute where, as is often the case, the medicament is hygroscopic. As a result, capsules must be packaged in secondary packaging such as a blister package, which significantly increases the overall bulk of the device. In addition, the secondary packaging can be unwieldy or difficult to open, particularly in an emergency situation where the medicine must be delivered as fast as possible under stressful circumstances.

Another disadvantage with the gelatin capsules is that they may become brittle. In this case, the piercing operation may produce shards or fragments that can be inhaled by the patient. In addition, gelatin is a material of biological origin and therefore often contains a certain amount of microbiological organisms, leading to possible contamination of the medicament.

Removal of the capsule from the secondary packaging and loading it into the device may require a degree of dexterity greater than that possessed by some patients. In addition, the motion of the elongate gelatin capsule within the device may be irregular, leading to incomplete or variable dispensing of the powdered medicament.

Other dry powder inhaler systems use foil based drug storage configurations. These systems also suffer from a variety of disadvantages. Many foil-based systems require complex manufacturing and filling processes. In addition, to open these foil based systems, external puncturing mechanisms, which can cause "dead spots" of trapped medication, are normally used.

Accordingly, an object of the invention to provide a capsule for delivery of powder or other medicaments while providing a barrier to moisture or other unwanted material that can degrade the medicament.

Another object of the invention is to provide a system for delivering a medicament in powder or liquid form that can use such a capsule without "dead spots" or complex manufacturing and filling requirements.

These and other objects and features of the invention will be apparent from the described description and the figures.

SUMMARY OF THE INVENTION

The present invention meets the foregoing objects by providing a sealed capsule with an integrated puncturing mechanism for storing and delivering a substance, such as a medicine. The capsule has two or more barrier layers forming a sealed chamber for containing the substance. An internal opening or puncturing mechanism is disposed within the capsule for puncturing a barrier layer defining the sealed chamber from within to release the substance from the chamber. The internal puncturing mechanism is adapted for puncturing the first chamber at a first location and, possibly a second location. If two locations are punctured, this creates an air path through the capsule.

The present invention features a sealed self-piercing capsule for storing and delivering a medicine. The capsule has a first layer formed of a first barrier material, a second layer formed of a second barrier material sealed at least in part to the first layer to form a sealed first chamber, and a second chamber disposed within the first chamber for holding the medicine. The second chamber is movable relative to the first layer and the second layers. The second chamber may include a first edge for puncturing at least one of the first and second layers.

The capsule may have a tube forming first chamber for holding the medicine, with an access hole at a first end and a first layer of barrier material covering the access hole. The first layer has a first portion that can be bonded at least in part to an outer surface of the tube and a second portion that is movable relative to the tube.

The capsule may be in the form of a tube forming a first chamber for holding the medicine which includes a first access hole at a first end and a second access hole at a second end. A first layer of barrier material is bonded at least in part to an outside surface of the tube, covering the first access hole and a second layer of barrier material bonded at least in part to the outside surface of the tube, covering the second access hole. A sharpened edge is formed on one of the first end and the second end of the tube for puncturing one of the first layer and the second layer. In an alternative mode, the tube may be formed of multiple "petals" which are closed in the first state but spread open, tearing the foil, in a second state.

The present invention also features a system for delivering a substance with a capsule that has a barrier material forming a chamber containing an amount of a substance to be delivered. The capsule includes an internal puncturing mechanism for opening the barrier material and releasing the substance to be delivered. The system also contains a delivery mechanism which has a first housing component configured to receive the capsule and an actuation mechanism for applying pressure to a first end of the capsule while the first housing component holds a second end of the capsule in a stationary position. The application of pressure to the first end of the capsule using the actuation mechanism causes the internal piercing mechanism to slide within the chamber, thereby actuating the internal puncturing mechanism.

The system for delivering a substance may also be in the form of a capsule having a barrier material forming a chamber containing an amount of a substance and including an internal puncturing mechanism for puncturing the barrier material to release the substance. The system also includes a delivery mechanism having a first housing component and a second housing component for housing the capsule. The second housing component is movable relative to the first housing component to actuate the internal puncturing mechanism.

DETAILED DESCRIPTION OF THE INVENTION

The present invention provides an improved capsule with an integrated puncturing mechanism for storing and delivering a substance, such as medicine. The enhanced sealing of the capsule promotes improved delivery of the substance by providing better protection of the substance from the elements, particularly if it is in the form of a powder, and improved opening the capsule to eliminate "dead spots.".

As used herein, the term "puncturing" refers to any form of opening, including piercing, perforating and tearing.

Figure 1:
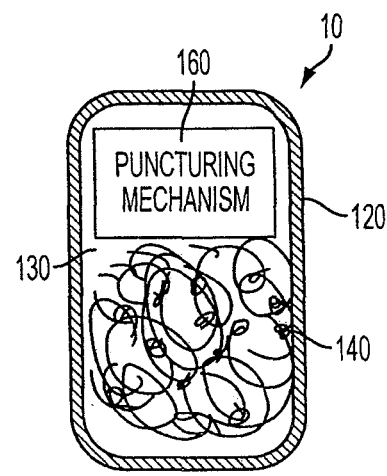
FIG. 1 illustrates a self-piercing capsule of an embodiment of the invention.

FIG. 1 illustrates a sealed, self-piercing capsule 100 for storing, protecting and delivering a substance, such as a medicine, suitable for use with a delivery system, such as an inhaler. Capsule 100, as shown in FIG. 1, comprises one or more layers of a barrier material 120 forming a sealed chamber 130 for holding a substance 140. The substance 140 stored in the capsule 100 can be in powder, fluid or solid form, and can comprise a medicine, chemical, or any suitable substance that requires protection from degrading elements. Barrier material 120 is preferably impervious to one or more elements, such as moisture and/or air, that tend to degrade the substance contained with the capsule. Examples of suitable barrier materials are moisture-impervious materials, including metal foil, such as aluminum or stainless steel foils, plastics and combinations thereof, and oxygen-impervious materials. Capsule 100 further includes an internal puncturing mechanism 160 disposed within chamber 130 for puncturing the barrier material 120 from within chamber 130 to create one or more openings for releasing substance 140 from capsule 100.

A capsule that is impervious to degrading elements, such as moisture and/or oxygen, provides significant advantages over gelatin capsules and other types of capsules. known in the art. The capsule provides protection of the substance from moisture and/or other degrading effects within the capsule, without requiring secondary packaging. The sealed capsule is preferably entirely sealed, i.e., it does not have any holes, until a user pierces or otherwise opens the capsule by actuating the internal puncturing mechanism 160 to puncture the capsule.

In addition to providing enhanced storage and protection of the substance, the barrier material 120 used to form sealed capsule 100 is lightweight, and not subject to the degradation which occurs in gelatin capsules. Sealed capsule 100 also has a much greater shelf life than gelatin and other prior medicine containers.

The use of an internal puncturing mechanism 160 further facilitates rapid opening of capsule 100, while protecting the contents of the capsule from exposure to degrading elements until actuation of internal puncturing mechanism 160. The capsule is self-contained and does not rely on external piercing components for accessing the substance stored therein. The internal puncturing mechanism allows opening of the capsule from the inside out which reduces dead spots.

Figure 2A:
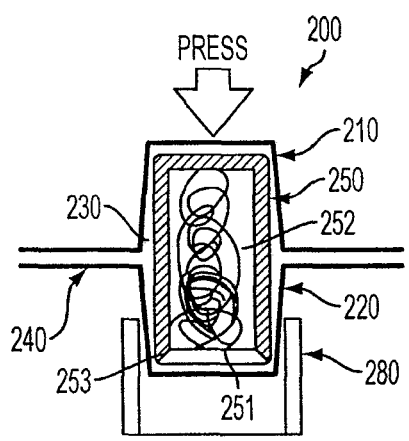
FIG. 2A illustrates a self-piercing capsule including an internal tube for puncturing an outer layer of the capsule.

FIG. 2A illustrates an embodiment of a sealed capsule 200, such as a moisture-impervious capsule for storing and delivering a medicine in powdered form. Sealed capsule 200 comprises a plurality of barrier layers, which can be formed of a moisture-impervious material such as foil or plastic. The barrier layers form a chamber, and an integrated puncturing mechanism disposed within the chamber for puncturing a barrier layer to open the capsule. Capsule 200 includes a first barrier layer 210, such as a layer of foil, which forms a lower chamber half and a second barrier layer 220, such as layer of foil, forming an upper chamber half. First layer 210 is bonded at least in part to the second layer 220, such that the lower chamber half and upper chamber half cooperate to form a hermetically sealed chamber 230 therebetween. As shown, a seal 240 is formed about the perimeter of chamber 230 between the first and second layers, which forms a sealed barrier between the chamber 230 and the ambient air.

Disposed within chamber 230 is a tube 250 defining an internal chamber 252 for containing a powdered medicine 260 or other substance. Initially, tube 250 is held within the chamber 230 by friction fit between the outer surface of the tube and each of the barrier layers 210, 220. The tube 250 can be located anywhere within chamber 230 by friction fit and is preferably movable relative to each of the barrier layers 210, 220. In FIG. 2A, tube 250 includes an access hole 251 for the internal chamber 252. The lower barrier layer 220 covers the access hole 251 and forms a powder seal against tube 250 to prevent the medicine from escaping the internal chamber 252.

In the embodiment shown in FIG. 2A, the access hole 251 comprises an opening formed in a first end of the tube 250. Alternatively, the tube 250 may be substantially closed at the first end and include a plurality of openings forming the access hole 251. Similarly, the access hole 251 may comprise one or more openings formed in the sidewall of the tube 250 in the vicinity of the first end. For example, the access hole 251 may comprise a plurality of holes formed about the perimeter of the tube 250 near the first end.

The tube 250 shown in FIG. 2A includes an integrated puncturing mechanism for puncturing one of the barrier layers to form an opening for releasing the medicine from the capsule 200. The illustrated puncturing mechanism comprises a sharpened edge 253 formed on the bottom edge of the tube 250. The sharpened edge 253 may be continuous about the bottom perimeter of tube 250, or may comprise one or more discrete edges formed at one or more locations on the tube. The puncturing mechanism is not limited to a sharpened edge and can comprise any suitable means, such as a chemical means, for puncturing one or more of barrier layers from the interior of the capsule or otherwise opening the capsule.

Figure 2B:
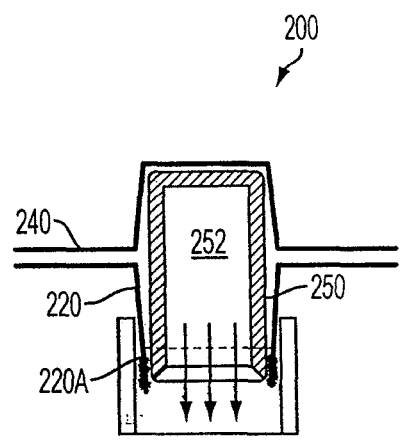
FIG. 2B illustrates the self-piercing capsule of FIG. 2A after opening of the capsule.

Tube 250 is slidable within the chamber 230 relative to the first layer 210 and the second layer 220, to actuate the puncturing mechanism to open the chamber 252. For example, as shown in FIGS. 2A and 2B, a barrel 280, which forms part of a delivery system for housing the capsule and delivering the substance contained therein, pushes against the lower layer 220 of the capsule 200 while pressure is applied to the opposite end of the capsule 200. Barrel 280 deforms the lower layer 220 to force lower layer 220 against the sharpened edge 253 of tube 250. One skilled in the art will recognize that any suitable device for pushing the lower layer 220 and/or the upper layer relative to the tube 250 may be used, and that the invention is not limited to the illustrative delivery system.

The barrel 280 shown in FIGS. 2A and 2B has an inner diameter configured to receive the lower end of capsule 200, though barrel 280 can have any suitable size and configuration. Barrel 280 and/or lower layer 220 are configured such that the coefficient of friction between the barrel 280 and the lower layer 220 is higher than the coefficient of friction between tube 250 and the lower layer 220. As a result, as barrel 280 moves toward the capsule 200, barrel 280 pushes the lower layer 220 against the sharpened edge 253 of tube 250. As barrel 280 continues to move forward, tube 250 moves within chamber 230 and toward lower layer 220, which causes the sharpened edge 253 to contact and puncture lower layer 220, thereby opening the capsule 200.

After puncturing the capsule 200, tube 250 pushes through the opening created by sharpened edge 253 and holds the punctured portion 220A of the lower layer 220 against the inner surface of barrel 280. As a result, the access hole 251 is maintained in an open position, facilitating the release of the medicine from within the capsule. The use of tube 250 to hold the punctured portion 220A of the capsule against the inner surface of the barrel also prevents shards of the punctured lower layer from traveling and being inhaled by a user. The punctured portion may be completely cut away from the lower layer 220, or may remain connected to the lower layer 220 through a non-punctured portion.

Capsule 200 thus protects and preserves the medicine, while providing easy release of the medicine by a user.

Figure 3A:
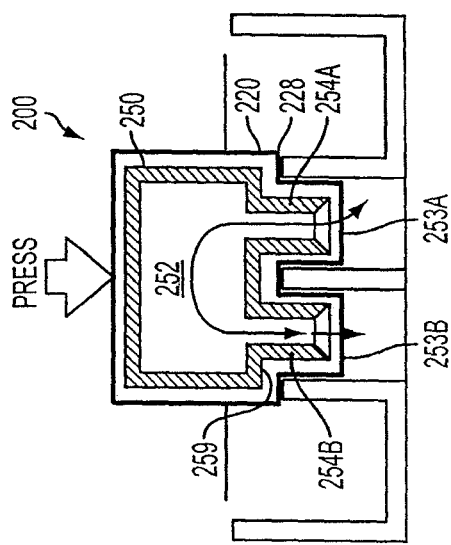
FIGS. 3A-3F illustrates embodiments a self-piercing capsule including a shoulder to facilitate actuation of the puncturing mechanism.

Lower layer 220 and/or barrel 280 may be configured to facilitate sliding of lower layer 220 relative to tube 250 to facilitate puncturing of the lower layer. For example, as shown in FIG. 3A, the lower layer 220 may include a shoulder 228 that surrounds at least a portion of the perimeter of tube 250. Shoulder 228 may be continuous about the entire perimeter of tube 250, or may comprise one or more discrete structures formed in lower layer 220. Shoulder 228 is configured to receive the top edge 281 of the barrel 280. Barrel 280 is sized and dimensioned to slide over lower portion of the lower layer 220, and abut shoulder 228. Top edge 281 of barrel 280 pushes against the shoulder 228 to push lower layer 220 past the sharpened edge 253 of the tube to puncture the capsule.

Figure 3B:
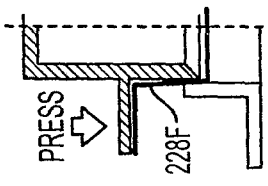
Figure 3C:
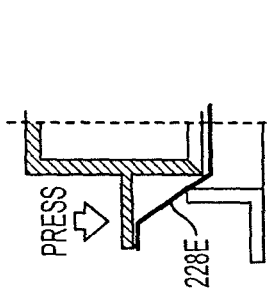
Figure 3D:
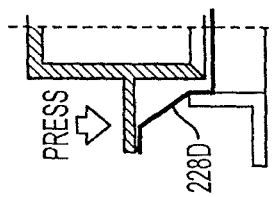
Figure 3E:
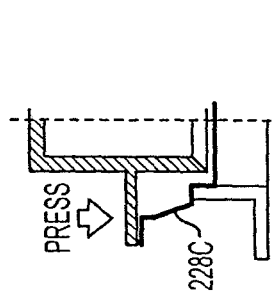
Figure 3F:
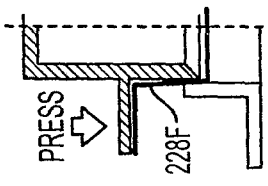

The shoulder can have any suitable geometry and is not limited to a shoulder that extends perpendicular to the tube 250. For example, the shoulder may be curved, angled or have any suitable configuration for abutting barrel 280. The shoulder may alternately be provided as a separate component, such as a ring attached around lower layer 220. Examples of alternate embodiments of shoulder 228 are shown in FIGS. 3B-3F. As shown in FIG. 3B, a shoulder 228C of a capsule can be slightly rounded. As shown in FIG. 3C, a shoulder 228C can be curved. As shown in FIG. 3D, a shoulder 228D may extend at an angle from the side of the capsule. As shown in FIG. 3E, a shoulder 228E can extend at an angle from the top of a capsule. As shown in FIG. 3F, a shoulder 228F can extend at a small angle relative to a tube 250 of the capsule. One skilled in the art will be able to determine a suitable configuration and size of a shoulder in a capsule having an integrated puncturing mechanism.

Alternatively, barrel 280 may be modified to increase the friction between lower layer 220 and barrel 280 to facilitate movement of lower layer 220 relative to tube 250 and thereby to facilitate puncturing of the lower layer. The inner surface of the barrel can be textured, or include protrusions or other features for gripping the lower layer to enhance the actuation of the puncturing mechanism.

Barrel 280 can also be advanced over the capsule end to puncture the capsule through a twisting action. For example, barrel 280 can include threads on the inner surface that engage with a protrusion formed on lower layer 220. As the barrel rotates, the threads engage the protrusion and advance the barrel, pushing the lower layer relative to tube 250. Alternatively, another threaded piece (not shown) is situated on the other side of the capsule that would engage barrel 280 and serve to force the capsule toward barrel 280 as the barrel is rotated.

Figure 4:
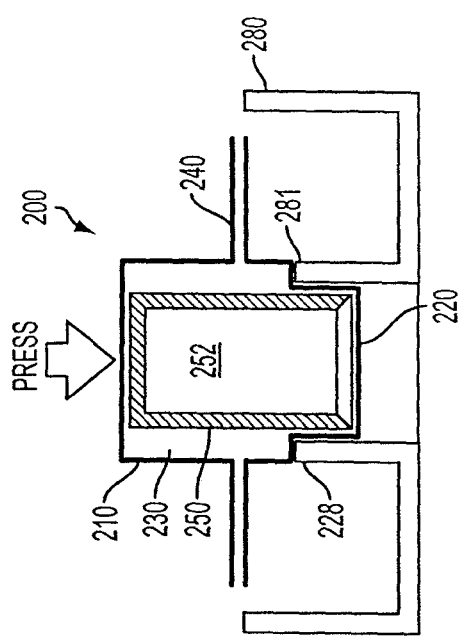
FIG. 4 illustrates a self-piercing capsule configured to form two openings on one end of the capsule.

The internal puncturing mechanism of the sealed capsule of the present invention may be configured to puncture the exterior layers of the capsules in a plurality of locations to create an air path through the capsule. For example, as shown in FIG. 4, tube 250 may include a first sharpened edge 253A and a second sharpened edge 253B for puncturing lower layer 220 in two different locations. The first punctured location forms an inlet to chamber 252, while the second punctured location can form an outlet for chamber 252. An airflow can be induced through chamber 252 to facilitate discharging of the medicine. In the embodiment of FIG. 4, first sharpened edge 253A and second sharpened edge 253B are each formed on a hollow tubular protrusion 254A, 254B, respectively, extending from chamber 252 toward lower layer 220. One skilled in the art will recognize that multiple inlets and/or multiple outlets may be formed to facilitate airflow through the capsule interior.

By creating an air path through the capsule, the puncturing mechanism reduces the dead volume of the capsule to ensure that the medicine does not get trapped within chamber 230. The use of the internal puncturing mechanism provides a clean access hole through the barrier material from the inside out, which eliminates the edges or other causes of "dead spots", ensuring that all of the medication stored in the capsule can be delivered. In addition, providing multiple openings provides a better airflow path and also helps to facilitate complete removal of the medicine from the capsule. The openings may further be designed to disperse the substance, for example a powder, as air moves through the chamber 252 by creating a vortex or turbulence.

In FIG. 4, tube 250 forms a flange 259 that is complementary to a shoulder 228 formed in the lower layer. Flange 259 limits travel of the tube relative to the first and second layers and/or the barrel 280, though tube 250 can also be formed without flange 259 and the capsule can be formed without shoulder 228.

Figure 5:
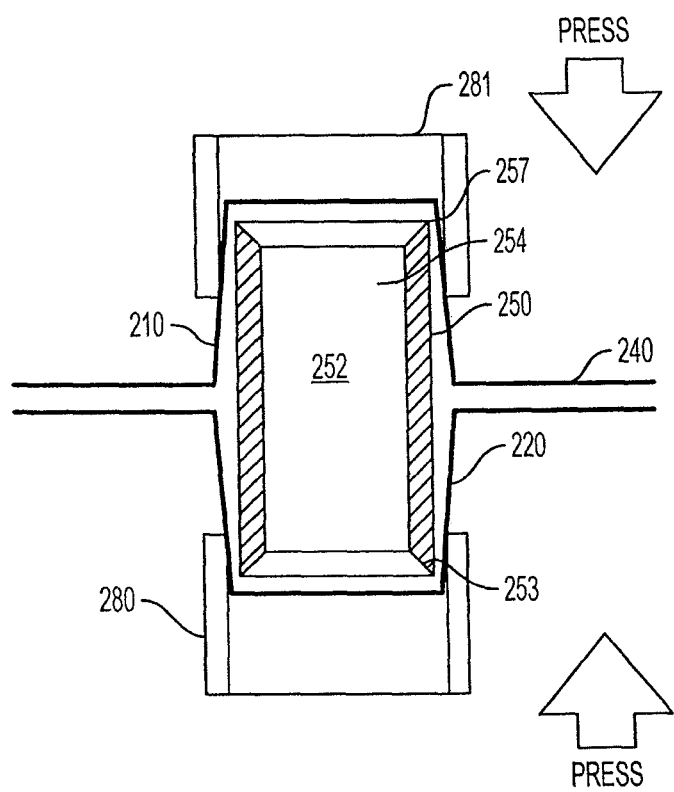
FIG. 5 illustrates a self-piercing capsule configured to form openings on opposite ends of the capsule.

Alternatively, the internal puncturing mechanism may be configured to puncture the capsule at opposite ends to create a flow-through air path through the capsule interior. For example, as shown in FIG. 5, tube 250 includes a second sharpened edge 257 on the end opposite the first sharpened edge 253 for puncturing the top layer 210 of the capsule. As shown, tube 250 may include a second access hole 254 formed at a second end of the tube 250. Prior to actuation of the puncturing mechanism, the second access hole 254 may be covered by the top layer 210 to seal the chamber 252. A second barrel 290 is provided for sliding the top layer 210 relative to tube 250, while first barrel 280 is used, as described above, to slide lower layer 220 relative to tube 250. As the barrels push against the capsule from opposite sides, tube 250 moves relative to both the upper and lower layers, such that first sharpened edged 253 punctures lower layer 220 and second sharpened edge punctures upper layer 210.

Figure 6A:
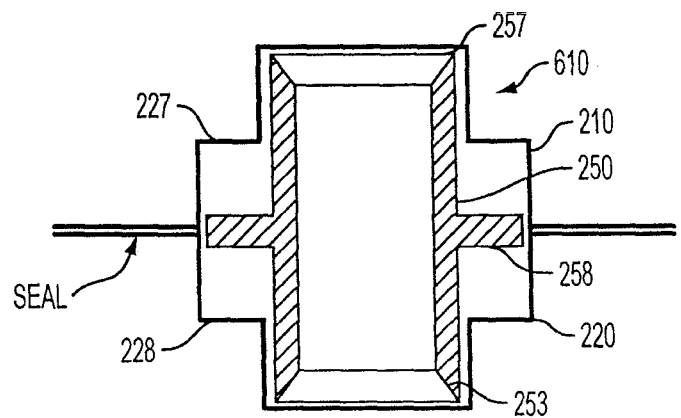
FIG. 6A illustrates a self-piercing capsule configured to form openings on opposite ends of the capsule and further including shoulders to facilitate opening of the capsule.

As shown in FIG. 6A, a capsule 610 configured to open on two opposite ends may also include shoulders 227, 228 formed in the first and second layers, respectively, about the perimeter of the tube 250 to facilitate movement of the tube relative to the two layers and thereby actuate a puncturing mechanism. In the embodiment of FIG. 6A, the tube also includes an annular protrusion 258 formed on at least a portion of the outer perimeter of tube 250. Annular protrusion 258 is configured to trap the first shoulder and/or the second shoulder to limit the travel distance of tube 250 relative to the barrier layer. Alternatively, the barrel can include a protrusion or other stop means for limiting the travel of tube 250.

Figure 6B:
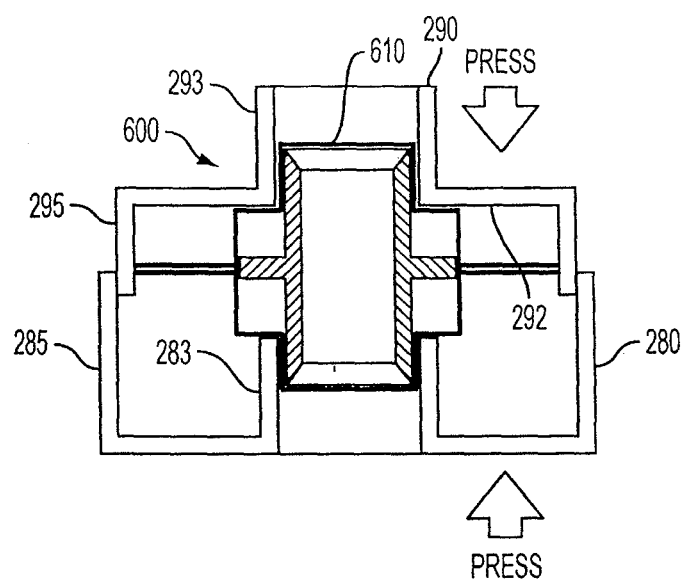
FIG. 6B illustrates a delivery system including the capsule of FIG. 6A.

FIG. 6B illustrates the capsule 610 of FIG. 6A in a delivery system 600, comprising a first barrel 280 and a second barrel 290. The first barrel and the second barrel cooperate to receive the capsule 610, such that a surface 292 of upper barrel 290 abuts the upper shoulder 227 of the capsule and a surface 282 of lower barrel 280 abuts the lower shoulder 228 of the capsule. As shown, lower barrel 280 may be configured to receive the upper barrel 290, for example, by having an outer wall 285 that has a diameter that is slightly larger than an outer wall 295 of the upper barrel. The upper barrel and the lower barrel also include inner tubular portions 283, 293, respectively, configured to receive a corresponding end portion of the barrel. Inner tubular portions 283, 293 preferably have an inner diameter that is slightly larger than the outer diameter of tube 250.

To open the capsule, pressure is applied to each barrel from opposite ends to push the barrels together. As the barrels are pushed together, surface 292 of the upper barrel pushes against shoulder 227 of top barrier layer 210, while surface 282 of the lower barrel pushes against shoulder 228 of lower barrier layer 220. The pressure applied to upper shoulder 227 causes top barrier layer 210 to move relative to tube 250. Top barrier layer 210 approaches the second sharpened edge 257 on the top side of the tube. As the barrel continues to move top barrier layer 210, the second sharpened edge 257 punctures the top barrier layer and pushes the tube through the resulting opening. Similarly, lower barrel 280 pushes lower barrier layer 220 until the lower sharpened edge 253 punctures lower barrier layer 220 and pushes the lower end of tube 250 through the resulting opening. Annular protrusion 258 forms a stop for limiting the travel of the barrels and preventing tube 250 and barrier layers 210, 220 from further movement. After actuation of the puncturing mechanism, tube 250 maintains an open air path through the capsule by pushing the punctured portions of the barrier layers against the interior wall of the respective barrel.

The capsule can be used with a delivery system, such as an inhaler. The released medicine can be inhaled directly through or from the storage chamber without having to transfer the medicine to another chamber for dispensing.

Figure 7A:
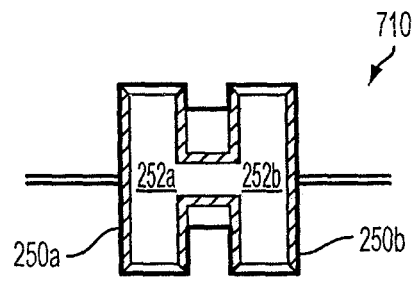
FIGS. 7A-7C illustrate embodiments of a self-piercing capsule that include a plurality of internal chambers.
Figure 7B:
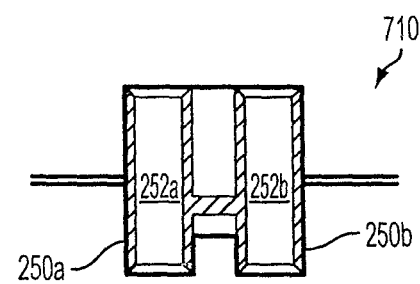
Figure 7C:
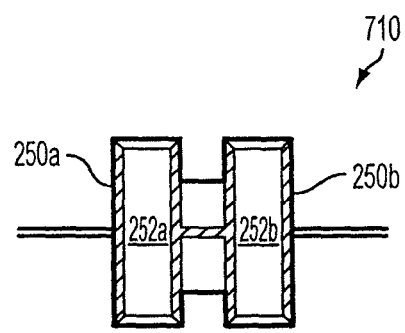

As shown in FIGS. 7A-7C, a capsule 710 may comprise a plurality of connected tubes 250A, 250B forming inner chambers 252A, B. The inner chambers 252A, 252B may be sealed and separate from each other, as shown in FIGS. 7B and 7C, or may be connected, as shown in FIG. 7A. The use of multiple chambers allows different substances to be stored and delivered together.

Figure 8A:
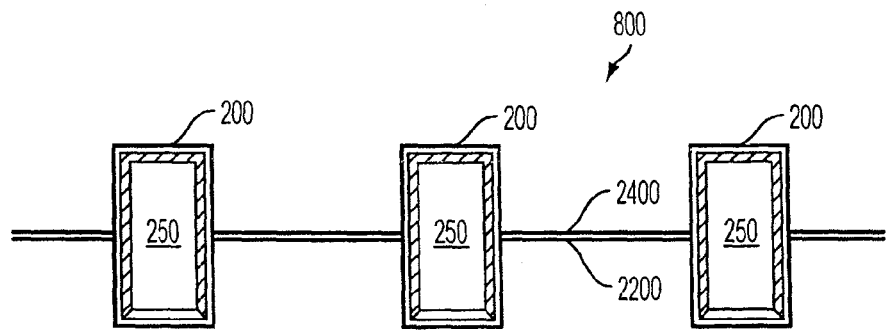
FIGS. 8A-8B illustrate a multi-dose strip of capsules.
Figure 8B:
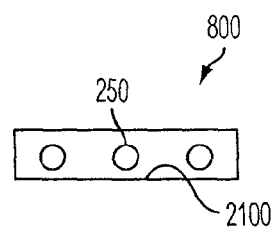

As shown in FIGS. 8A and 8B, a plurality of single-dose capsules 200 may be provided together in a strip 800. Strip 800 comprises a plurality of discrete tubes 250 and an integrated top barrier layer 2100 and a bottom barrier layer 2200 connecting tubes 250.

Figure 9:
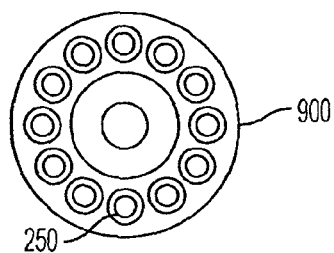
FIG. 9 illustrates a disk containing a plurality of capsules each with doses of medicine.

As shown in FIG. 9, a plurality of doses of a medicine, where each dose is stored in a tube 250, can be provided as a disk 900.

Figure 10:
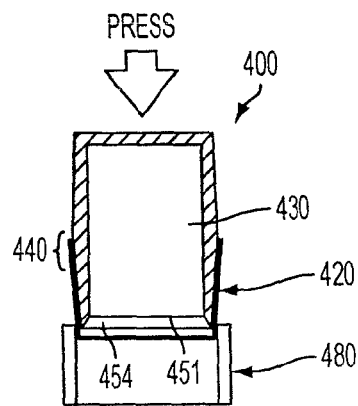
FIG. 10 illustrates a self-piercing capsule including a barrier layer bonded to a tube.

FIG. 10 illustrates another embodiment of a sealed capsule 400 including an integrated puncturing mechanism. Capsule 400 includes a tube 450 forming a chamber 430 for holding medicine or another substance therein. Tube 450 includes an access hole 451 on the first end, which is covered by a layer 420 of a barrier material, such as a moisture-impervious material. A portion of barrier material 420 is bonded, at least in part, to the outside surface of tube 450 to form a seal 440 about the periphery of the tube. The seal 440 hermetically seals the chamber 430 from the outside environment to protect the substance contained therein from exposure to damaging elements. The remainder of the barrier material 420 is not bonded to tube 450 and is movable relative to tube 450. Capsule 400 includes an integrated puncturing mechanism, illustrated as a sharpened edge 454 formed on the first end of the tube, for puncturing layer 420 to open the capsule 400. The sharpened edge 454 punctures barrier material 420 when the unbonded portion of the material slides past the end of tube 450.

According to one aspect of the invention, at least a portion of the tube can be formed of a transparent material to allow a user to view the contents of chamber 430. Having a transparent portion or window allows the user to see if the drug has been contaminated or clumped before inhalation, thereby minimizing some potential problems common with many inhalers. Similarly, the user can see if all of the medication has been dispensed by viewing through the window post-inhalation.

Barrel 480 may be used to actuate the puncturing mechanism by moving the unbonded portion of barrier material 420 relative to tube 450. As the barrel pushes the unbonded portion of barrier material 420, sharpened edge 454 advances toward the material 420. The sharpened edge 454 punctures and pushes through the material 420 to open chamber 430.

Figure 11A:
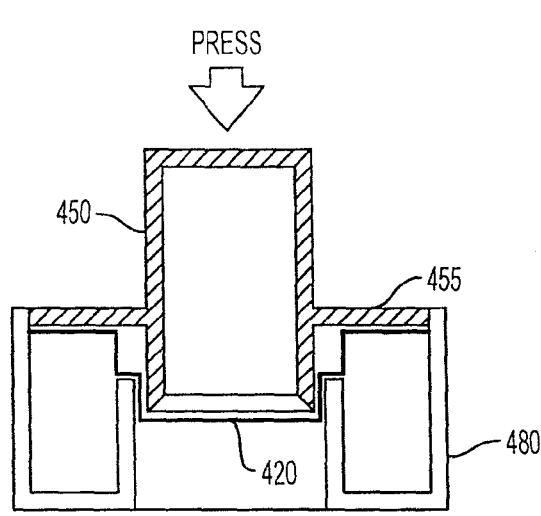
FIG. 11A illustrates a self-piercing capsule including a barrier layer bonded to a flange on a tube.
Figure 11B:
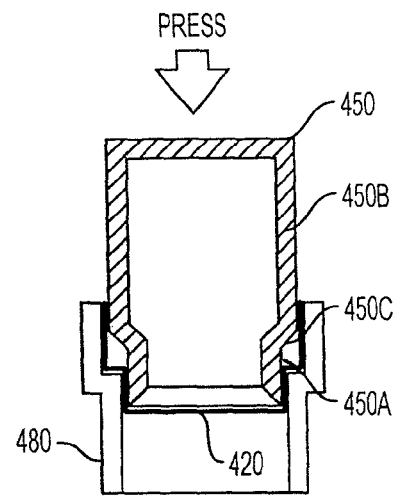
FIG. 11B illustrates a self-piercing capsule including a barrier layer bonded to a stepped outer surface on a tube.

As shown in FIGS. 11A and 11B, the barrier material 420 can be bonded to a protrusion on tube 450, which also serves to limit the travel of barrel 480. For example, as shown in FIG. 11A, the barrier material can be bonded to a flange 455 extending about the perimeter of tube 450. After puncturing of the barrier layer, the flange forms a stop for the top edge 481 of the barrel to prevent the capsule from sliding through the barrel interior.

Alternatively, as shown in FIG. 11B, the tube may include a lower section 450A having a first diameter, a second section 450B having a second, larger diameter, and a step 450C connecting the first and second sections. The barrier material is bonded to the second section 450B, and the step is configured to limit the travel of the barrel 480, which has an inner surface configured to interface with the capsule outer surface. In addition to limiting the travel of barrel 480, step 450C provides a bonding surface for the foil.

In the embodiments of FIGS. 11A and 11b, barrier layer 420 forms a shoulder 448 to facilitate sliding of the unbonded portion relative to the tube, though the capsule can alternatively be formed without the shoulder.

Figure 12:
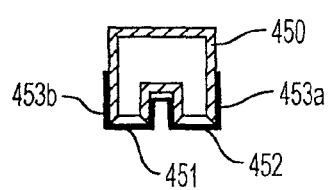
FIG. 12 illustrates a self-piercing capsule including a barrier layer bonded to an outer surface on a tube having a plurality of access holes on one side.

Sealed capsule 400 may also be configured to be punctured in a plurality of locations to create a flow path through the tube. For example, as shown in FIG. 12, tube 450 may include a plurality of access holes 451, 452 on one side. Tube 450 is similar to the embodiment shown in FIG. 4, and includes a plurality of edges 453A, 453B for puncturing the barrier layer in the vicinity of the access holes to open the capsule. While the embodiment of FIG. 12 shows the barrier layer bonded to an outer surface of tube 450, the barrier layer can also bond to a flange or other protrusion on the outer surface of the tube, as described above. The barrier layer can also include a shoulder or other suitable configuration for facilitation sliding of the unbonded portion relative to the tube to puncture the barrier layer.

Figure 13:
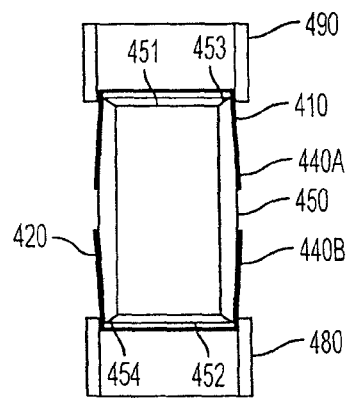
FIG. 13 illustrates a self-piercing capsule including a plurality of barrier layers bonded to opposite ends of a tube and including an integrated puncturing mechanism configured to form openings on opposite sides of the capsule.

Alternatively, the puncturing mechanism may be configured to create openings on opposite ends of the sealed capsule, as shown in FIG. 13. For example, the capsule shown in FIG. 13 includes a first access hole 451 formed on a first end of tube 450, and a second access hole 454 formed on a second end of the tube. First access hole 451 is covered by a first barrier layer 410, which bonds at least in part to the outside surface of tube 450 to form a first seal 440A. The second access hole 452 is covered by a second barrier layer 420, which bonds at least in part to the outside surface of the tube to form a second seal 440B. The first and second seals form a hermetically sealed chamber 430 within tube 450. Tube 450 also includes a first sharpened edge 454 formed along at least a portion of the perimeter of first access hole 451 for puncturing the first barrier layer. Tube 450 also includes a second sharpened edge 458 formed along at least a portion of the perimeter of second access hole 452 for puncturing the second barrier layer.

The unbonded portion of first barrier layer 410 is movable relative to tube 450 to facilitate puncturing of the capsule. The unbonded portion of second barrier layer 420 may also be movable relative to tube 450 to facilitate puncturing of the capsule. To puncture capsule 400 to release a substance contained within chamber 430, an upper barrel 490 pushes against first barrier layer 410 to push the unbonded portion of first barrier layer 410 against sharpened edge 454, while the bonded portion of first barrier layer 410 is held stationary against the tube outer surface. The upper barrel 490 moves the unbonded portion of first barrier layer 410 until the sharpened edge punctures the first barrier layer to create an opening. Barrel 490 may continue to push first barrier layer 410 past the sharpened edge to push tube 450 through the resulting opening. Similarly, a lower barrel 480 pushes the unbonded portion of second barrier layer 420 toward second sharpened edge 458 to cause the second sharpened edge to puncture and create an opening in second barrier layer 420. The puncturing of the first and second barrier layers may occur simultaneously or at separate times.

One of ordinary skill in the art will recognize that the delivery system is not limited to the described barrels, and that any suitable means can be used to house and/or actuate the puncturing mechanism. For example, the user could actuate a puncturing mechanism by pushing directly on one of the barrier layers with his fingers to slide the puncturing mechanism relative to the barrier layer in order to puncture the capsule.

As described above, the use of a plurality of different sharpened edges to create a plurality of openings in a capsule create an air path through the capsule to facilitate release of the substance contained therein.

Figure 14A:
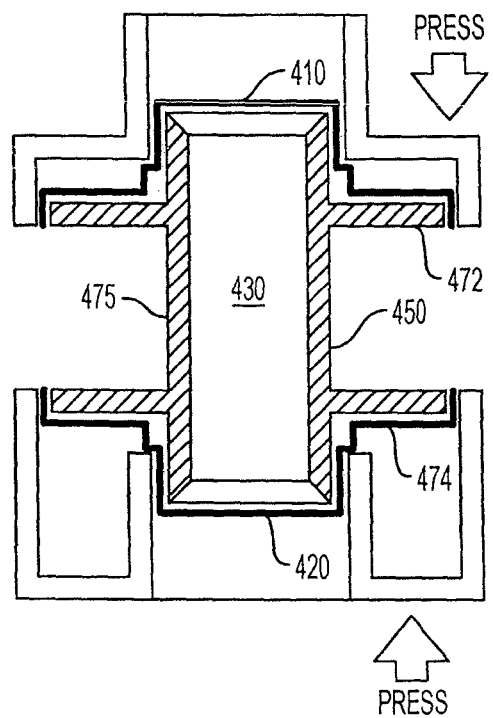
FIG. 14A illustrates a self-piercing capsule including a plurality of barrier layers bonded to flanges formed opposite ends of a tube and including an integrated puncturing mechanism configured to form openings on opposite sides of the capsule.
Figure 14B:
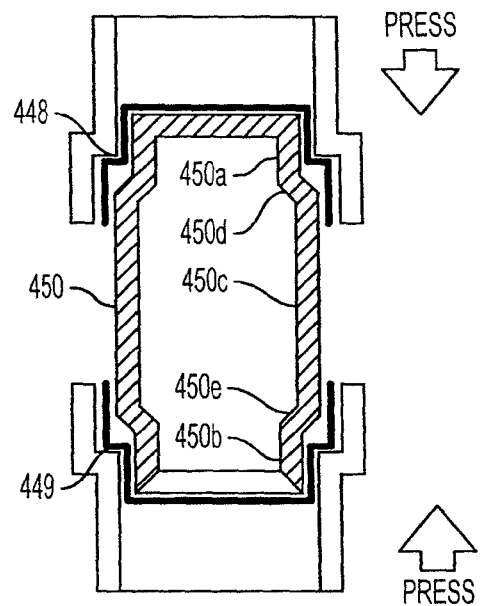
FIG. 14B illustrates a self-piercing capsule including a plurality of barrier layers bonded to a stepped outer surface on an end of a tube and including an integrated puncturing mechanism configured to form openings on opposite sides of the capsule.

As shown in FIGS. 14A and 14B, one or both of the barrier layers can be bonded to a protrusion, flange or other feature on the outer surface of tube 450. For example, as shown in FIG. 14A, upper barrier layer 410 may be bonded to an upper flange 472 and lower barrier layer 420 may be bonded to a lower flange 474. The flanges may form a stop for limiting the travel distance of tube 450 relative to the barrels and the barrier layers. The portion of the tube between the flanges may form a window 475 to allow a user to view the contents of the chamber 430. For example, tube 450 or a portion of the tube between the flange may be formed of a transparent material to create the window.

In FIG. 14B, the end portions 450A, 450B of tube 450 have a diameter that is reduced relative to the central portion 450C.

A step 450D, 450E connects the central portion 450C to each of the end portions 450A, 450B, respectively. Steps 450D, 450E also form stops for limiting the travel of the barrels relative to tube 450.

In the embodiments of FIGS. 14A and 14B, the upper and lower barrier layers further include shoulders 448, 449, respectively, to facilitate movement of the unbonded portion relative to the tube, though the capsule can also be formed without the shoulder or using other means to facilitate movement of the unbonded portion relative to the tube. The barrier layers may alternatively be bonded to opposite sides of a central flange or protrusion on tube 450.

A plurality of capsules 400 or chambers 450 may be provided together as a strip or a disk to provide a multi-dose package. The different doses may be linked by the barrier material, or by the material forming the tube, for example, by flanges extending from each of the tubes.

In many of the embodiments of the invention, the capsule including an integrated puncturing mechanism may be configured to spin about a central axis to facilitate ejection of the substance from the capsule. For example, after puncturing of the barrier material, the capsule can spin to eject medicine from therein and cause the medicine to be entrained in airflow to be inhaled by the user.

Figure 15A:
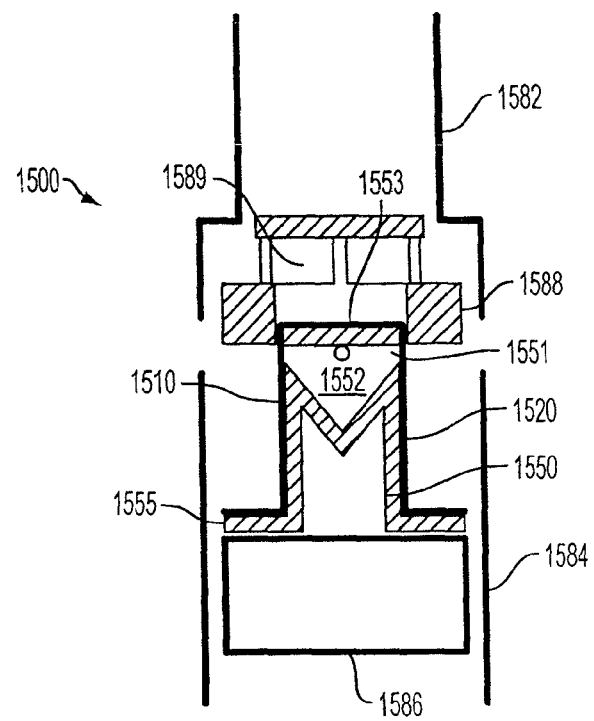
FIGS. 15A-15B illustrate a delivery system including a rotatable fan for a self-piercing capsule configured to spin within the delivery system to facilitate release of a substance contained therein according to an embodiment of the invention.
Figure 15B:
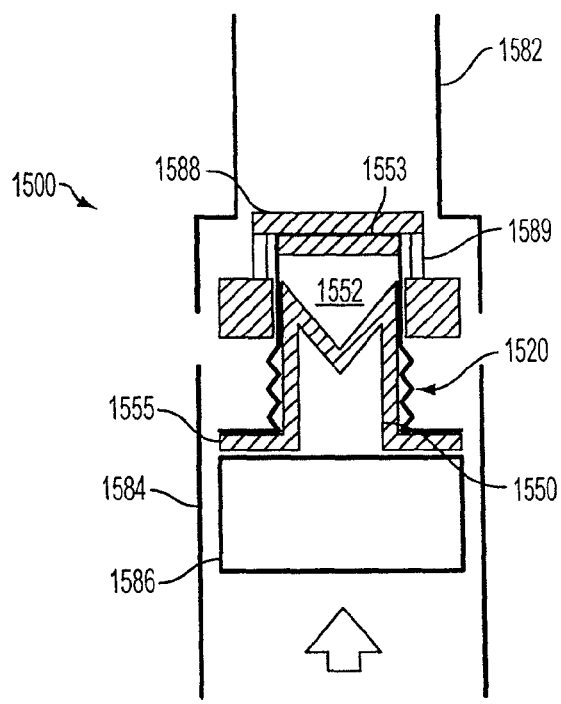

FIGS. 15A and 15B illustrate a delivery system 1500 including a capsule 1510 having an integrated puncturing mechanism that is configured to spin about a central axis to facilitate ejection of a medicine from the capsule after puncturing of the capsule. As shown, the capsule 1510 comprises a tube 1550 defining an inner chamber 1552 for containing a medicine or other substance. The tube 1550 includes one or more access holes 1551 for providing access to the inner chamber 1552. The access holes 1551 are shown as being formed in the side wall of the tube 1550 at an upper end of the tube. The capsule 1510 further includes a barrier material 1520 bonded at least in part to the tube 1550 and covering the access holes 1551 to seal the chamber 1552. The chamber 1552 may have a conical shape, as shown, to facilitate ejection of the medicine through the access holes 1551 when the capsule spins about a longitudinal axis.

In the illustrative embodiment, the barrier material 1520 is bonded to a flange 1555 formed on the tube 1550, though one skilled in the art will recognize that the barrier material 1520 can be bonded to any suitable location or component of the tube 1550.

The capsule 1510 further includes an integrated puncturing mechanism, which comprises a sharpened edge 1553 formed about the perimeter of the upper end of the tube in the embodiment shown in FIGS. 15A and 15B.

The capsule 1510 is configured to be disposed in a delivery system 1500 comprising a mouthpiece 1582, a holder 1584, a plunger 1586 and a radial fan 1588. The radial fan 1588, which fits inside the mouthpiece 1582, forms a ring that surrounds the top end of the capsule 1510 when the delivery system 1500 is assembled. The plunger, which fits inside the holder 1584, forces the capsule 1510 against the radial fan. To open the capsule, as shown in FIG. 15B, the user pushes the mouthpiece 1582 and the holder 1584 together. As the mouthpiece 1582 moves toward the holder 1584, the mouthpiece pushes the radial fan 1588 against the plunger 1586. The radial fan 1588 contacts and pushes against the barrier material 1520, which deforms the barrier material and causes the barrier material to slide against the internal puncturing mechanism, i.e., the sharpened edge 1553, to open the capsule.

Figure 15C:
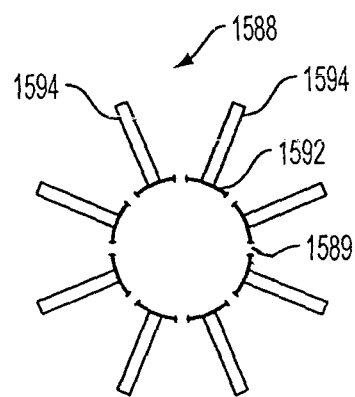
FIG. 15C is a top view of the rotatable fan of the delivery system of FIGS. 15A and 15B.

FIG. 15C is a cross-sectional top view of the radial fan 1588. As shown, the radial fan 1588 comprises a central ring 1592 configured to receive the upper end of the capsule 1510. Fan blades 1594 extends about the circumference of the radial fan to cause rotation of the fan when air passes past the fan 1588. Fluted air vents 1589 provide an air path through the radial fan to allow air flow from the holder to the mouthpiece.

At the same time, or shortly thereafter, the user inhales air through the mouthpiece 1582 to create an air flow through the inhaler. As air moves through the inhaler, fluted blades on the radial fan 1588 cause the radial fan to spin, which in turn causes the capsule 1510 to spin. As the capsule spins, centrifugal force acts on the substance in the chamber 1552 to expel the substance out of the chamber through the now-opened access holes 1551. The blades of the radial fan 1588, in addition to inducing the spinning of the capsule, further break up the substance to facilitate inhalation of the substance by the user. The inhaler body can also include fluted air vents to help direct air flow onto the fan blades to cause the rotation.

The capsule 1510 can also be configured to open in a plurality of locations to allow air flow through the capsule, which can facilitate the expulsion of the substance in addition to the centrifugal force.

Figure 16A:
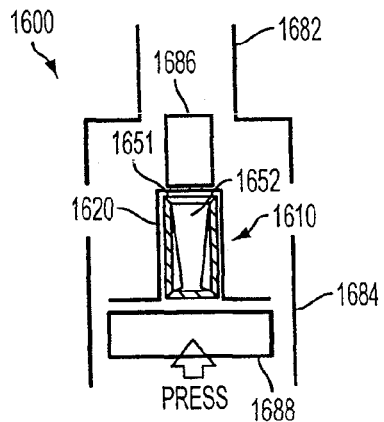
FIGS. 16A-16B illustrate a delivery system for implementing a self-piercing capsule configured to form fan blades for rotating the capsule when the capsule is opened.
Figure 16B:
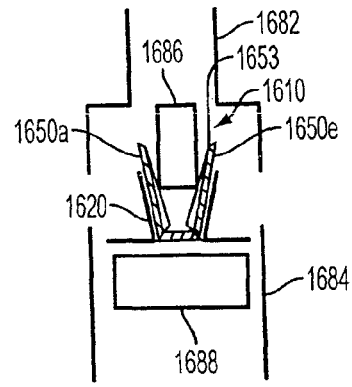

In an alternate embodiment, a capsule including an integrated puncturing mechanism can be configured to form a plurality of fan blades when the capsule opens to facilitate release of the substance stored therein. FIGS. 16A and 16B illustrate a delivery system 1600 suitable for use with a capsule 1610 including integrated fan blades. The capsule 1610 includes a tube 1650 forming an internal chamber 1652 for containing a substance. A barrier material 1620 covers the tube 1650, including a top hole 1651 of the tube 1650, to seal the capsule. The delivery system 1600 includes a mouthpiece 1682, a holder 1684, an anvil 1686 coupled to and movable relative to the mouthpiece 1682 and a plunger 1688 for pushing a capsule 1610 disposed within the delivery system 1600 against the anvil 1686.

To open the capsule 1610, the user pushes the mouthpiece 1682 toward the holder 1684, which pushes the anvil 1686 into the top hole 1651 and against the barrier material 1620 of the capsule 1610. As the anvil 1686 pushes against the barrier material 1620, sharpened edges on the tube 1650 puncture the barrier material 1620 to open the capsule. The anvil continues to press against the capsule to spread blades 1650*a*, 1650*b* forming the tube 1650 open. The spreading of the blades 1650*a*, 1650*b* opens the capsule by piercing and tearing the barrier material 1620.

Figure 17A:
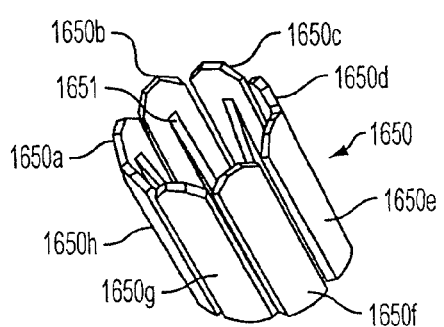
FIGS. 17A-17C illustrate a tube forming an inner chamber of a self-piercing capsule, the tube configured to form a plurality of fan blades when the capsule is opened.
Figure 17B:
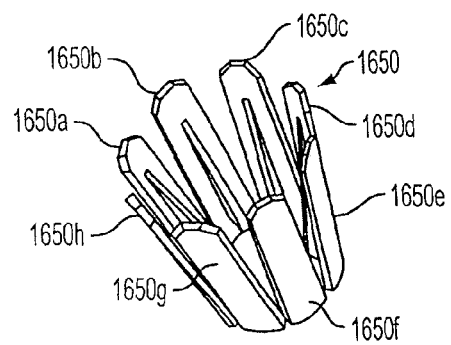
Figure 17C:
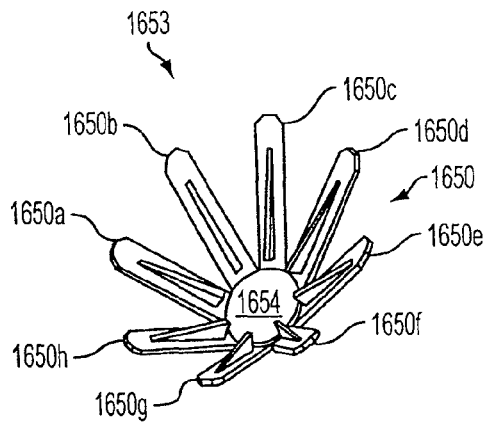

As shown in FIGS. 17A-17C, the tube 1650 comprises a plurality of hinged blades 1650*a*-1650*h*, connected to a bottom surface 1654. One or more of the blades includes a sharpened upper edge 1653 for puncturing the barrier material 1620. FIG. 17A illustrates the tube 1650 defining the internal chamber 1652 of the capsule 1610 when the capsule is in a closed, sealed position. FIG. 17B illustrates the tube 1650 in a semi-opened position, when the blades 1650*a*-1650*h* are slightly spread. In the fully opened position, shown in FIG. 17C and FIG. 16B, the blades 1650*a*-1650*h* form fluted air vents, which allow the substance to escape the capsule. As a user inhales air through the mouthpiece, the generated airflow causes the blades to rotate, thus rotating the capsule about a longitudinal axis. Alternatively, the blades 1650*a*-1650*h* serve only to open the capsule, and other fan blades, for example fan blades on a radial fan, such as the radial fan of FIG. 15C can be used to effect rotation of the capsule 1610.

The rotation of the capsule facilitates the release and entrainment of the substance in the airflow and creates a vortex effect to facilitate delivery of the substance to the user. Alternatively, the capsule can be configured to form flutes in the barrier material upon puncturing of the capsule, which can act as fan blades to induce rotation of the capsule. Alternatively, the capsule and/or barrier material can be manufactured with integral fan blades to facilitate rotation, rather than forming the fan blades during the puncturing process.

In the embodiments of FIGS. 15-17, the self-piercing capsule including the integrated puncturing mechanism spins within a delivery system to facilitate delivery of a substance using air flow generated by a user. Alternatively, a mechanical device, such as a motor, may be used to spin the capsule to facilitate delivery of a substance contained in the capsule.

Figure 18A:
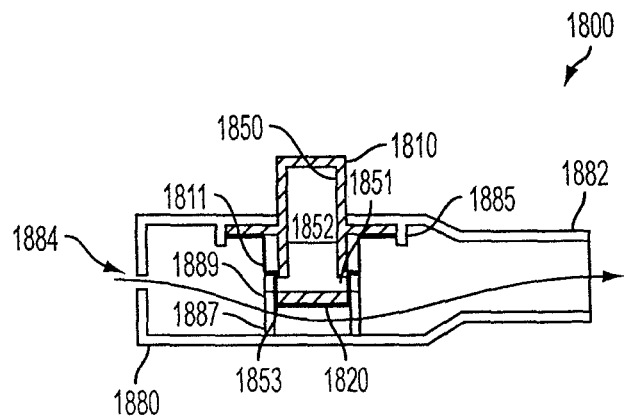
FIGS. 18A-18B illustrate an inhaler for delivering a medicine stored in a self-piercing capsule according to another embodiment of the invention.
Figure 18B:
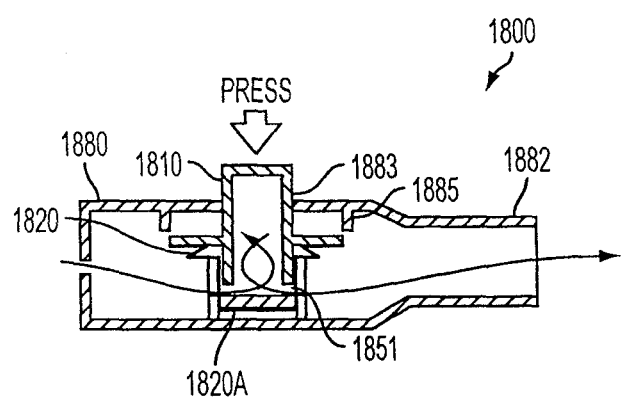

FIGS. 18A and 18B illustrate an inhaler suitable for implementing a capsule including an internal puncturing mechanism according to the invention. The inhaler 1800 comprises a housing 1880 forming a mouthpiece 1882 and including an air inlet 1884 opposite the mouthpiece 1882. The mouthpiece 1882 can alternatively be configured to be inserted or interface with a user's nasal passage for inhalation via the nose. The housing 1880 forms an air path between the inlet and the mouthpiece. The housing 1880 is configured to hold a capsule 1810 containing a substance and including an internal puncturing mechanism. As shown, the housing holds the capsule 1810 in a position such that an air path through the punctured capsule intersects the air path through the housing 1880.

Capsule 1810 is similar to the capsule shown in FIG. 11A, except the access holes 1851 are formed in a side wall of the tube 1850 defining the capsule chamber 1852 for holding the substance. The capsule 1810 includes a barrier material 1820 covering the access holes 1851. A portion of the barrier material 1820 is bonded in part to the tube 1850 to seal the capsule chamber 1852, while an unbonded portion is movable relative to the tube 1850. Tube 1850 includes a sharpened edge 1853 formed on a lower end thereof to facilitate opening of the capsule 1810. As shown, the barrier material 1820 forms a shoulder 1811 to facilitate sliding of the barrier material 1820 past the sharpened edge 1853 to puncture the barrier material.

The housing 1880 includes a capsule hole 1883 sized and dimensioned to receive the capsule, an upper protrusion 1885 on an inner surface of the housing surrounding the capsule hole for receiving the flange of the capsule, and a lower protrusion 1887 configured to abut the shoulder 1811 of the capsule 1810 to hold the capsule 1810 within the housing.

When the user presses against the upper end of the capsule 1810, as shown in FIG. 18B, the capsule 1810 moves within the housing toward the lower protrusion 1887. The lower protrusion 1887 presses against the shoulder 1811 to prevent movement of the barrier material 1820, while allowing the tube 1850 to slide relative to the barrier material. As the capsule is pressed into the bottom of the housing 1880, the barrier material 1820 buckles, and the sharpened edge of the capsule 1810 punctures the barrier material. The punctured portion 1820A of the barrier material 1820 forms a disk in the shape of the sharpened edge 1851, which is trapped between the capsule and the housing 1880.

As shown in FIG. 18B, after puncturing of the capsule 1810, the access holes 1851 of the capsule align with air vents 1889 on the lower protrusion 1887 to allow the substance to escape the capsule. Alternatively, the air vents 1889 are provided in fluid communication with the access holes 1851 to provide an air path between the air inlet 1884 and the mouthpiece 1882 through the punctured capsule 1810. As the user inhales through the mouthpiece 1882, drawing air into the housing interior via the air inlet and through the capsule 1810 via the access holes 1851, the air vents 1889 direct the airflow through the capsule to disperse the powder into the inhaled air for delivery to the user.

Figure 19:
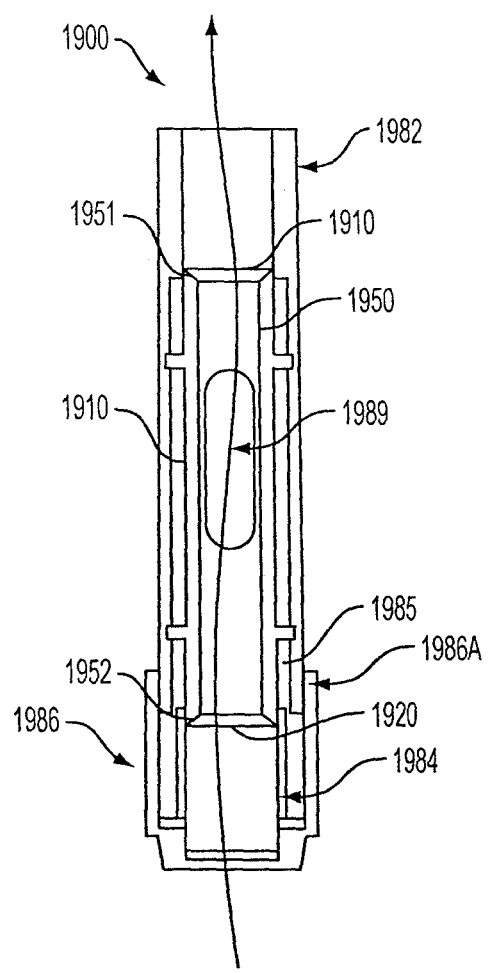
FIG. 19 illustrates an inhaler for delivering a medicine stored in a self-piercing capsule configured to open at two ends to form a flow-through air path according to another embodiment of the invention.

FIG. 19 illustrates another delivery system suitable for implementing a capsule having an integrated puncturing mechanism. The delivery system 1900 is suitable for use with a capsule 1910 comprising an open-ended tube 1950 covered on each side by a barrier material 1910, 1920, for example as shown in FIG. 14A. Delivery system 1900 includes a first housing component, illustrated as a mouthpiece 1982, and a second housing component 1984 coupled to the first housing component. Delivery system 1900 also includes a threaded cap 1986 surrounding the second housing component 1984 and including threads 1986a on an inner surface thereof for engaging threads on an outer surface of the mouthpiece 1982. The capsule 1910 is disposed in a chamber 1985 formed by the housing components, such that the first barrier material 1910 abuts an inner surface of the mouthpiece 1982 and the second barrier material 1920 abuts an inner surface of the second housing component. As shown in FIG. 19, the capsule is held within the chamber 1985 via friction fit.

To actuate the inhaler and open capsule 1910, the threaded cap 1986 is twisted to force the mouthpiece 1982 and the second housing component 1984 closer together. As the mouthpiece 1982 and second housing component 1984 move closer together, each housing component pushes the adjacent barrier material 1910, 1920 relative to the tube 1950, causing sharpened edges 1951, 1952 on each end of the tube 1950 to puncture the barrier material 1910, 1920 to create a flow through air path through the capsule 1910. The user inhales through the mouthpiece 1982 to pull the substance within the capsule into the user's lungs.

The mouthpiece 1982 can be configured for a user's mouth or nose, so that the user can inhale the substance through the mouth or nose in this, and all other embodiments of the invention.

In the delivery system of FIG. 19, one of the housing components, illustrated as the mouthpiece 1982 includes a transparent window 1989 aligned with a transparent portion of the capsule 1910 to allow the user to view the substance to ensure complete delivery of the substance to the user.

The sealed capsule of the present invention provides significant advantages not seen in the prior art. The capsule provides a sealed, protected environment for a substance and prevents exposure of the substance from degrading elements for an extended period of time. For example, the capsule can provide a moisture-impervious environment for moisture-sensitive substances, such as medicines in powdered form. The use of an integrated, internal puncturing mechanism facilitates release of the substance from the capsule without relying on external components. The puncturing mechanism may be easily actuated, for example, by sliding the puncturing mechanism (i.e., the tube) within the internal chamber of the capsule. The components of the sealed capsule are designed for manufacturability and the capsule may be assembled and filled quickly and efficiently. The integrated puncturing mechanism of the invention provides a clear, unobstructed path for the substance stored in the capsule to exit and reduces the number of dead spots or edges that trap the substance, a feature common in capsules that utilize external puncturing mechanisms. Moreover, the ability to create an air path through an internal chamber of a capsule using an integrated puncturing mechanism allows direct delivery of the substance from the capsule, without requiring transfer of the substance to a separate delivery chamber. The integrated puncturing mechanism facilitates complete evacuation of all of the substance from the capsule interior, resulting in more accurate dosing, increased safety and reduced waste.

The present invention has been described relative to illustrative embodiments. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A dose inhaler device, comprising:
    a sealed first chamber including a first layer of barrier material, the first layer of barrier material having a shoulder and covering one or more access holes into the first chamber;
    an internal puncturing mechanism within the first chamber, the internal puncturing mechanism having a surface adjacent to a portion of the first layer;
    a dose for inhalation located in the first chamber; and
    a barrel having a first inner surface with a first inner surface size and a shape arranged to receive at least part of the internal puncturing mechanism to enable piercing of the first layer by cooperation of the barrel and the internal puncturing mechanism,
    wherein a portion of the first layer conforms to the surface of the internal puncturing mechanism and movement of the internal puncturing mechanism relative to the barrel pierces the first layer and exposes the one or more access holes.

2. The device of claim 1, wherein the internal puncturing mechanism is bonded to the first layer.

3. The device of claim 1, wherein the shoulder at least partially surrounds the internal puncturing mechanism.

4. The device of claim 1, wherein the internal puncturing mechanism includes an edge arranged to completely cut a punctured portion of the first layer from remaining portions of the first chamber.

5. The device of claim 1, wherein the barrel defines at least part of a flow path into which at least part of the dose is introducible.

6. The device of claim 1, wherein the internal puncturing mechanism and the barrel have cylindrical surfaces that contact each other to position the internal puncturing mechanism and the barrel relative to each other.

7. The device of claim 1, further comprising a housing having a mouthpiece, an air inlet, and an air path that extends from the air inlet to the mouthpiece,
    wherein movement of a part of the first layer into the barrel pierces the first chamber such that a portion of air in the air path can enter and exit the first chamber via the one or more access holes.

8. The device of claim 7, wherein the first chamber is arranged to move in a direction transverse to the air path to cause the internal puncturing mechanism to pierce the first layer.

9. The device of claim 8, wherein a portion of the first chamber protrudes from the housing and is depressable by a user to move the first chamber in the direction transverse to the air path.

10. The device of claim 9, wherein the first chamber includes a cylindrically shaped capsule with the one or more access holes formed on cylindrical sidewall of the capsule.

11. The device of claim 10, wherein the first layer covers an end of the capsule and extends along a portion of the cylindrical sidewall to cover the one or more access holes.

12. The device of claim 11, wherein an end portion of the capsule forms the internal puncturing mechanism.

13. The device of claim 10, wherein the capsule includes a flange that extends from the cylindrical sidewall.

14. The device of claim 13, wherein the housing includes a capsule hole for receiving an end of the capsule with the flange positioned outside of the capsule hole.

15. The device of claim 1, wherein the internal puncturing mechanism includes a flow-through air path through which air and dose is flowable to exit the first chamber with the first layer pierced to expose the one or more access holes.

* * * * *